(12) United States Patent
Yang

(10) Patent No.: US 7,488,310 B2
(45) Date of Patent: Feb. 10, 2009

(54) SANITARY NAPKIN INCLUDING A MOISTURE SENSITIVE STABILIZING LAYER

(75) Inventor: Morris Yang, Princeton Junction, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 40 days.

(21) Appl. No.: 11/550,238

(22) Filed: Oct. 17, 2006

(65) Prior Publication Data

US 2008/0091158 A1    Apr. 17, 2008

(51) Int. Cl.
*A61F 13/20* (2006.01)
(52) U.S. Cl. .................. 604/385.01; 604/358; 604/355; 604/385.31; 604/378; 604/385.01
(58) Field of Classification Search ................ 604/358, 604/355.1, 385.31, 378, 385.1, 385.01
See application file for complete search history.

(56) References Cited

U.S. PATENT DOCUMENTS

| | | | | | |
|---|---|---|---|---|---|
| 3,117,577 | A | * | 1/1964 | Mosier | 604/399 |
| 5,578,025 | A | * | 11/1996 | May | 604/385.31 |
| 6,007,528 | A | * | 12/1999 | Osborn, III | 604/387 |
| 6,306,123 | B1 | * | 10/2001 | Salerno et al. | 604/385.31 |
| 6,613,031 | B2 | * | 9/2003 | Glasgow et al. | 604/385.03 |
| 6,821,269 | B1 | * | 11/2004 | Boulanger et al. | 604/385.04 |

* cited by examiner

*Primary Examiner*—Tatyana Zalukaeva
*Assistant Examiner*—Ilya Y Treyger

(57) ABSTRACT

An absorbent article including a cover layer, a barrier layer, and a stabilizing layer arranged between said cover layer and said barrier layer. The stabilizing layer has a Dry Stiffness Index of at least about 0.9 g/gsm and a Wet Stiffness Loss of at least about 80%.

19 Claims, 3 Drawing Sheets

SANITARY NAPKIN INCLUDING A MOISTURE SENSITIVE STABILIZING LAYER

FIELD OF THE INVENTION

The present invention generally relates to sanitary absorbent articles and in particular to feminine sanitary napkins which exhibit an increase in flexibility in the wet state.

BACKGROUND OF THE INVENTION

Externally worn, sanitary napkins are one of many kinds of feminine protection devices currently available. The development of materials having a high liquid absorption capacity per unit volume has allowed the required overall thickness of sanitary napkins to be reduced, thereby providing a product which is more comfortable and less obtrusive to wear. Thin, flexible, sanitary napkins of this type are disclosed, for example, in U.S. Pat. No. 4,950,264 to T. W. Osborne III.

Applicants have found that it can be difficult to handle thin, flexible, absorbent articles such as sanitary napkins. The very properties that make them desirable in use (e.g., high flexibility), can make them difficult to handle and place into position prior to use. For example, a thin, flexible sanitary napkin having positioning adhesive thereon, may tend to fold onto itself, causing the positioning adhesive to prematurely stick to other surfaces of the sanitary napkin, thereby rendering the napkin unsuitable for use.

As such, applicants have recognized there is a need for absorbent articles that are easy to handle and place into position against the undergarment prior to use, but are also thin and highly flexible during use.

SUMMARY OF THE INVENTION

According to a first aspect of the invention, the present invention provides an absorbent article including a cover layer, a barrier layer, a stabilizing layer having dimensions, the stabilizing layer arranged between the cover layer and the barrier layer and having a Dry Stiffness Index of at least about 0.9 g/gsm and a Wet Stiffness Loss of at least about 80%, a first portion located outside the dimensions of the stabilizing layer, a second portion located within the dimensions of the stabilizing layer, the first portion having an MCB Stiffness less than an MCB Stiffness of the second portion.

According to a second aspect of the invention, the present invention provides an absorbent article including a cover layer, a barrier layer, an absorbent system arranged between the cover layer and the barrier layer, a stabilizing layer including a mixture of fibrous material and a water-soluble binder, the fibrous material present in the amount of from about 50% to about 90% by weight and the water-soluble binder present in an amount of from about 10% to about 50% by weight, a first portion located outside the dimensions of the stabilizing layer, a second portion located within the dimensions of the stabilizing layer, the first portion having an MCB Stiffness less than an MCB Stiffness of the second portion, and the stabilizing layer having a Dry Stiffness Index of at least about 0.9 g/gsm and a Wet Stiffness Loss of at least about 80%.

BRIEF DESCRIPTION OF THE DRAWINGS

Examples of embodiments of the present invention will now be described with reference to the drawings, in which.

DETAILED DESCRIPTION OF THE INVENTION

Figure 1:
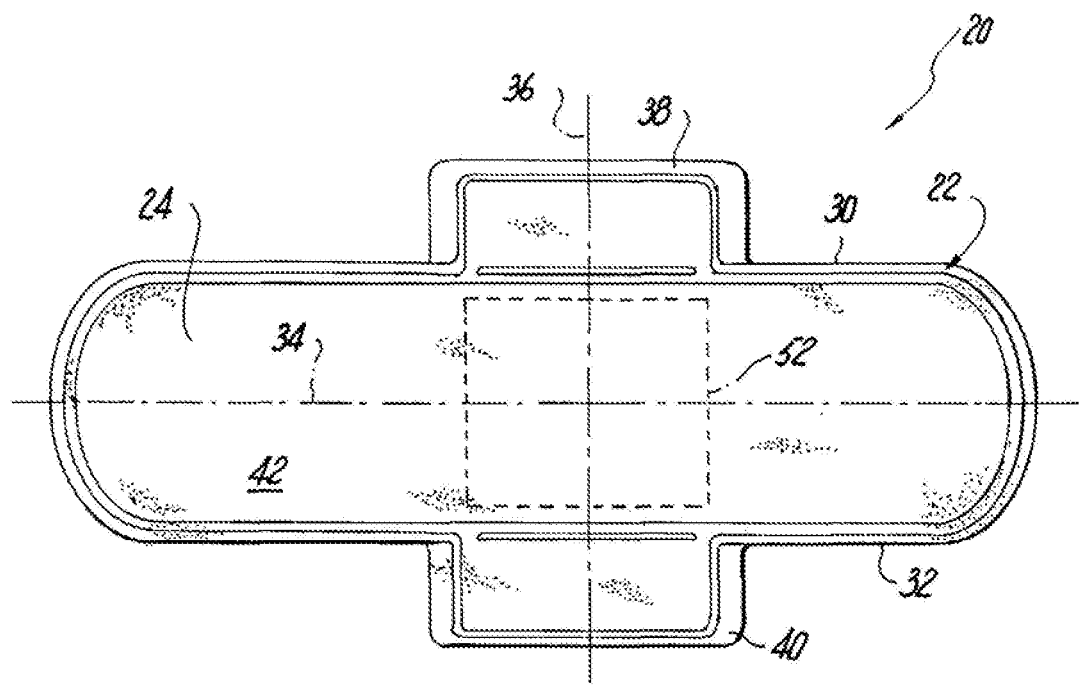
FIG. 1 is a top plan view of a sanitary napkin in accordance with a first embodiment of the present invention.

The present invention provides a sanitary napkin that is highly flexible and absorbent during use, yet is also convenient and easy to place in the undergarment prior to use. The sanitary napkin includes a stabilizing layer that helps provide structural integrity when the napkin is in the dry state. The stabilizing layer allows the user to easily handle the napkin and thereby facilitates the application of the napkin to the undergarment prior to use. The stabilizing layer employed in the present invention undergoes a loss in stiffness (i.e. a Wet Stiffness Loss defined herein) upon exposure to moisture, thereby enabling the sanitary napkin to also provide excellent comfort to the user during use.

Sanitary napkins according to the present invention include a first portion located outside the dimensions of the stabilizing layer and a second portion located within the dimensions of the stabilizing layer. Preferably, the first portion of the sanitary napkin, i.e. the portion located outside the dimensions of the stabilizing layer, is highly flexible in the dry state. "Highly flexible" as used herein means having a flexural resistance, i.e. an MCB Stiffness as defined herein, of less than 400 g, preferably less than 250 g and most preferably less than 150 g. The second portion of the sanitary napkin, i.e. the portion located within the dimensions of the stabilizing layer, is sufficiently stiff in the dry state to enable the user to easily handle and place the napkin in the undergarment prior to use. "Sufficiently stiff" as used herein means an MCB Stiffness of greater than 400 g.

Sanitary napkins according to the present invention are preferably thin, preferably having a thickness of less than 4.0 mm, more preferably less than 3.0 mm, and most preferably less than 2.5 mm.

Referring to FIGS. 1-5, there is shown a first embodiment of the present invention, a feminine sanitary napkin 20. The sanitary napkin 20 has a main body 22 with a first transverse side 26 defining a front portion thereof and a second transverse side 28 defining a rear portion thereof. The main body also has two longitudinal sides, namely a longitudinal side 30 and a longitudinal side 32.

Figure 2:
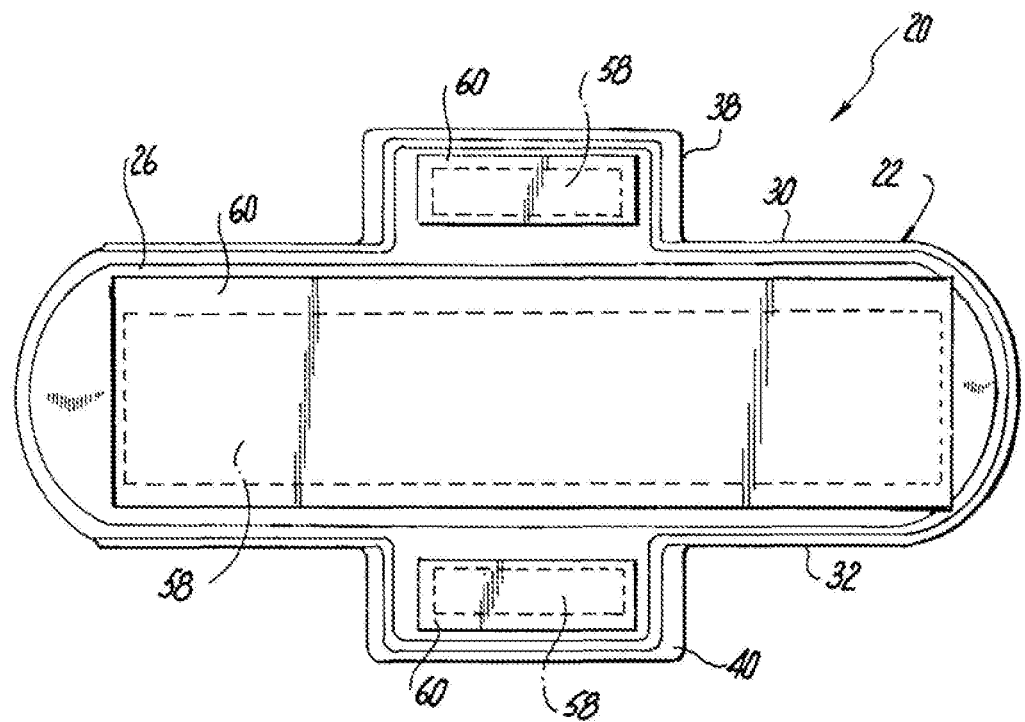
FIG. 2 is bottom plan view of the sanitary napkin of FIG. 1.

The sanitary napkin 20 has a longitudinal centerline 34 that bisects the sanitary napkin 20 in two identical halves. Projecting laterally outward from each of the longitudinal sides 30, 32 are flap 38 and flap 40 respectively. The main body 22 also has an imaginary transverse centerline 36 arranged perpendicular to the longitudinal centerline 34 that bisects flaps 38, 40. FIG. 2 depicts a bottom plan view of the sanitary napkin shown in FIG. 1.

Figure 3:
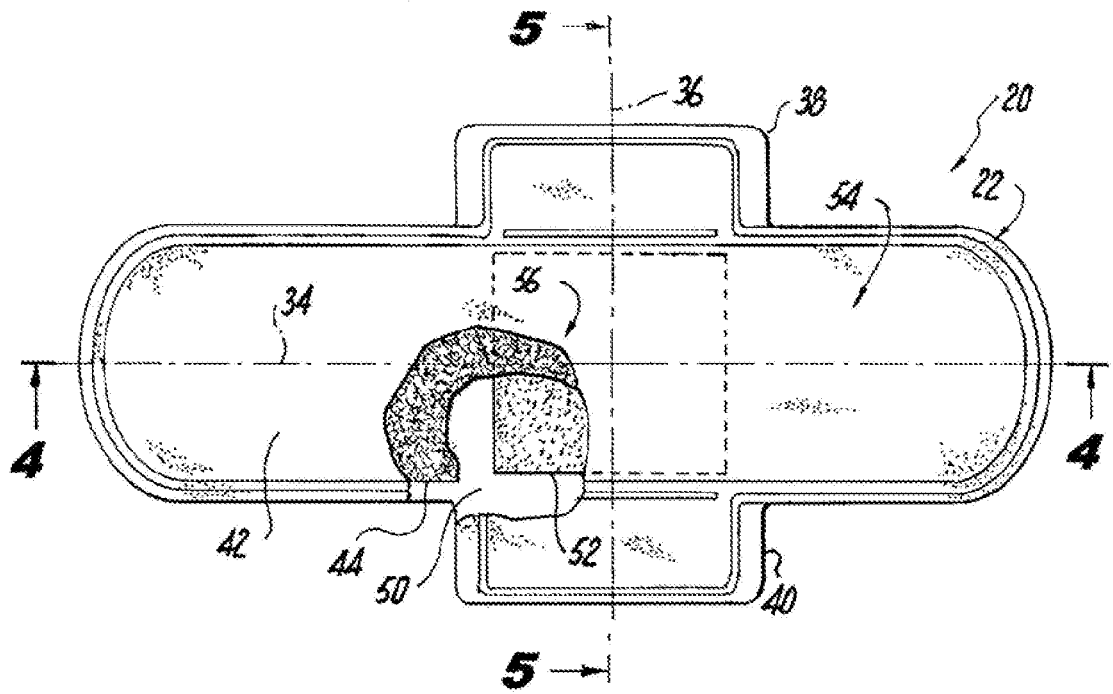
FIG. 3 is a top plan view of a sanitary napkin shown in FIG. 1, with the cover layer and absorbent system thereof partially broken away to reveal the stabilizing layer.
Figure 4:
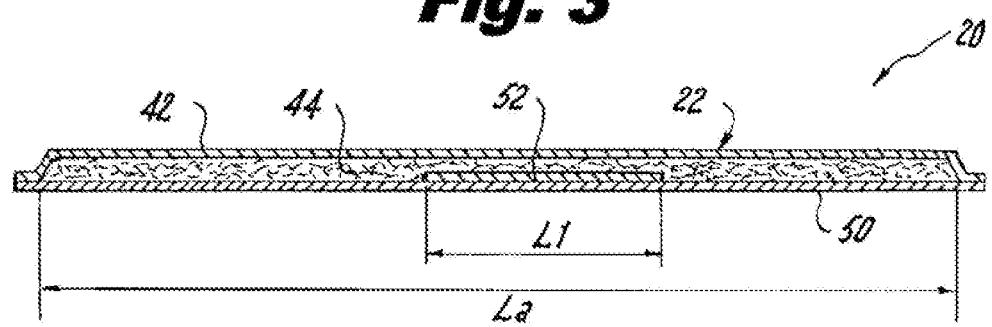
FIG. 4 is a sectional view of the sanitary napkin of FIG. 3, taken along the longitudinal center line 4-4 thereof.
Figure 5:
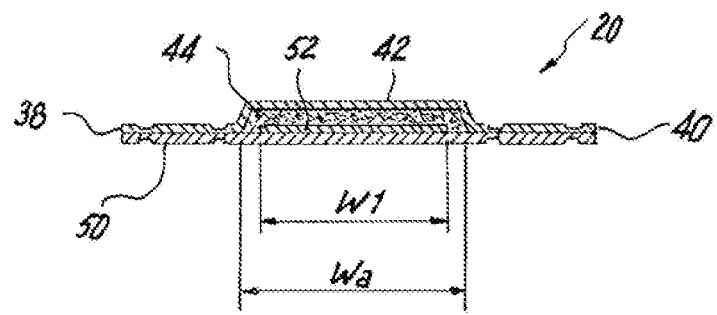
FIG. 5 is a sectional view of the sanitary napkin of FIG. 3, taken along the transverse centerline line 5-5 thereof.

As shown in FIGS. 3-5, the main body 22 is of a laminate construction and comprises a fluid-permeable cover layer 42, a fluid-impervious barrier layer 50, and a stabilizing layer 52 arranged between the cover layer 42 and the barrier layer 50. As best seen in FIG. 2, barrier layer 50 includes, on a garment facing surface thereof, garment attachment adhesive 58 for securing the napkin to an undergarment during use. The adhesive 58 is covered with removable release paper 60 prior to use.

The stabilizing layer 52 is "sensitive" to moisture, more particularly the stiffness of the stabilizing layer is significantly reduced upon exposure to bodily fluid such as menses. The main body 22 may further comprise an optional absorbent system 44.

The material for the stabilizing layer 52 is selected such that the napkin 20 has an MCB Stiffness, in the dry state, that is greater within the dimensions of the stabilizing layer 52, i.e. within second portion 56, than outside the dimensions of the stabilizing layer 52, i.e. within the first portion 54. Thus, the napkin 20 will have at least a first MCB Stiffness value, in the dry state, outside the dimensions of the stabilizing 52 and a second MCB Stiffness value, in the dry state, within the dimensions of the stabilizing layer 52, the first MCB Stiffness value being less than the second MCB Stiffness value. Preferably the second MCB Stiffness value is greater than 400 g. The MCB Stiffness values of the first portion 54 and the second portion 56 may be determined by the "Procedure for Measuring Modified Circular Bend Stiffness (MCB) of a Sanitary Article" set forth herein.

The stabilizing layer 52 is designed to provide sufficient stiffness to the napkin 20 when the napkin 20 is in a dry state such that a user can readily handle and position the sanitary napkin 20 prior to use. The stabilizing layer 52 further functions to assume a low stiffness when it absorbs liquid, e.g., menses. As such, during use, the napkin 20 is highly flexible and therefore comfortable to the user.

In order to impart sufficient dry stiffness to the sanitary napkin 20 to enable easy handling in the dry state, it is necessary that the stabilizing layer 52 extend over a sufficient portion of the sanitary napkin 20. However, it is also desirable that the stabilizing layer 52 extend over a relatively small area of the sanitary napkin 20 such that the sanitary napkin 20 retains its overall flexibility in the dry state. The inventors have found that the stabilizing layer 52 desirably covers from about 5% to about 50% and most preferably from about 10% to about 25% of the optional absorbent system 44. The area of the absorbent system 44 that the stabilizing layer 52 "covers" is measured by laying the sanitary napkin flat upon a firm surface. The fraction of the area of the stabilizing layer 52 is measured relative to the area of absorbent system 44 of the napkin. Alternatively, if no separate absorbent system 44 exists, i.e. if the absorbent article only includes a cover layer 42 and a barrier layer 50, then the fraction of the area of the stabilizing layer 52 is measured relative to the entire area of the absorbent portion of sanitary napkin, e.g. the area of the napkin excluding the area defined by the garment attaching wings or flaps of the napkin if such wings or flaps are present.

Various configurations are possible for arranging the stabilizing layer 52 relative to the other components of the sanitary napkin 20. FIGS. 1-5 depict one preferred configuration for a stabilizing layer 52. In this embodiment, the stabilizing layer 52 is arranged between the absorbent system 44 and the barrier layer 50. As such, the stabilizing layer 52 does not retard the movement of fluid into the absorbent system 44. Furthermore, in this particular embodiment, the stabilizing layer 52 is a transversely extending strip (the boundaries of which are shown in phantom in FIG. 1) that has a length L1 and a width W1. In the embodiment of the invention shown in FIGS. 1-5, L1=W1 or W1>L1.

In the embodiment of the invention shown in FIGS. 1-5, L1 has a length that is less than a length La of the absorbent system 44. Thus, in this embodiment, the napkin generally has a first portion 54 that is located outside the dimensions of the stabilizing layer 52 and a second portion 56 located within the dimensions of the stabilizing layer 52.

L1 may range from about 5% of La to about 30%, preferably from about 10% of La to about 25% of La. Although one may choose a length of the stabilizing layer 52 according to the particular length of the sanitary napkin 20, a suitable length of the stabilizing layer may be, for example, from about 10 mm to about 70 mm, preferably from about 25 mm to about 55 mm, more preferably from about 30 mm to about 50 mm.

In the embodiment of the invention shown in FIGS. 1-5, W1 is less than or equal to a width Wa of the absorbent system 44. For example, W1 may range from about 100% to about 50% of Wa, preferably from about 70% to about 100% of Wa.

Figure 6:
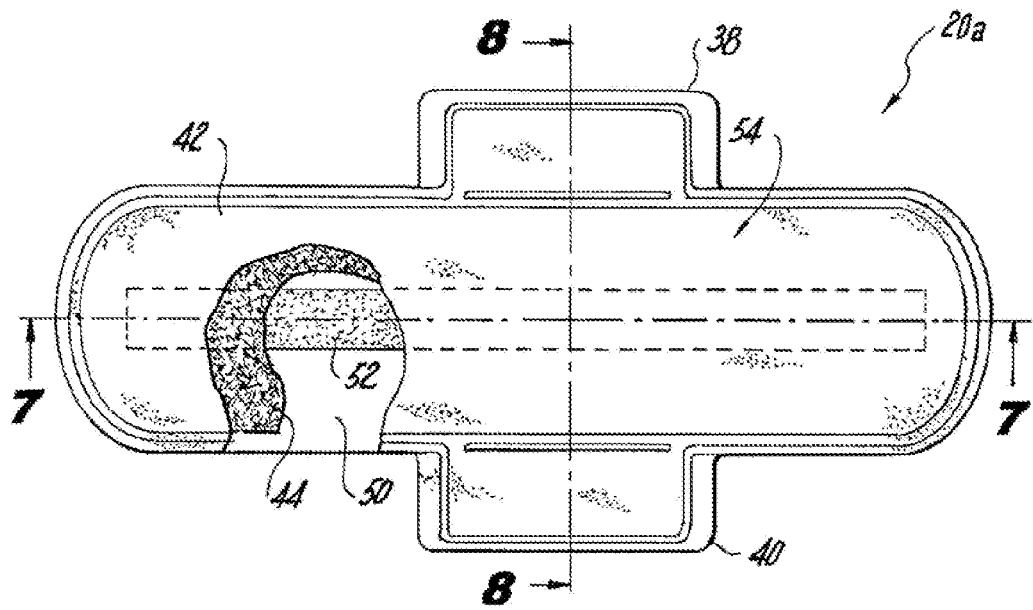
FIG. 6 is a top plan view of a sanitary napkin in accordance with another embodiment of the present invention, with the cover layer and absorbent system thereof partially broken away to reveal the stabilizing layer.
Figure 7:
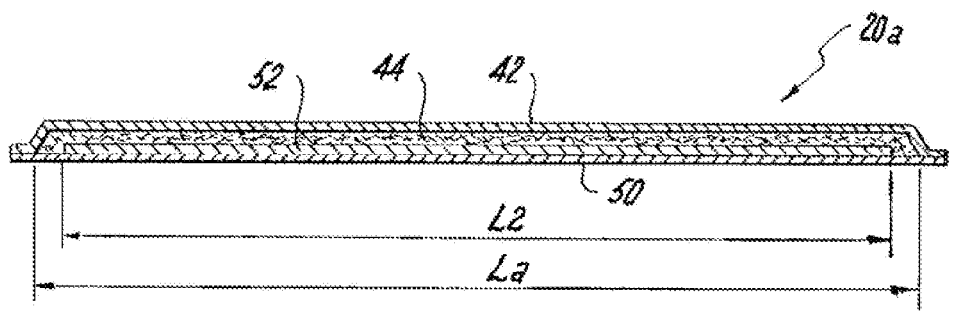
FIG. 7 is a sectional view of the sanitary napkin of FIG. 6, taken along the longitudinal center line 7-7 thereof.
Figure 8:
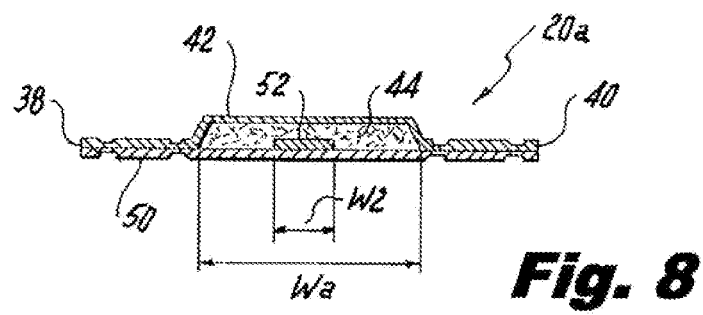
FIG. 8 is a sectional view of the sanitary napkin of FIG. 6 taken along the transverse center line 8-8 thereof.

FIGS. 6-8 depict a sanitary napkin 20a according to another embodiment of the present invention in which the stabilizing layer 52 is again positioned between the absorbent system 44 and the barrier layer 50, but the stabilizing layer 52 is a longitudinally extending strip (the boundaries of which are shown in phantom in FIG. 6) The stabilizing layer 52 has a length L2 and a width W2. In the embodiment of the invention shown in FIGS. 6-8, L2>W2.

In the embodiment of the invention shown in FIGS. 6-8, W2 has a length that is less than a width Wa of the absorbent system 44. Thus, in this embodiment, the napkin generally has a first portion 54 that is located outside the dimensions of the stabilizing layer 52 and a second portion 56 located within the dimensions of the stabilizing layer 52.

W2 may range from about 5% of Wa to about 90%, preferably from about 10% of Wa to about 50%. Although one may choose a width, W2 of the stabilizing layer 52 according to particular width of the sanitary napkin 20, a suitable width of the stabilizing layer 52 may be, for example, from about 10 mm to about 40 mm, preferably from about 10 mm to about 35 mm, more preferably from about 15 mm to about 30 mm.

In the embodiment of the invention shown in FIGS. 6-8, L2 has a length that is less than or equal to a length La of the absorbent system 44. For example, L2 may range from about 100% to about 50% of La, preferably from about 75% to about 100% of La.

While FIGS. 1-5 and FIGS. 6-8 depict the stabilizing layer 52 arranged between the absorbent system 44 and the liquid-impervious barrier 50, in another embodiment, the stabilizing layer 52 may be arranged between the absorbent system 44 and the cover layer 42. However, in such an embodiment, the stabilizing layer 52 should be configured and include materials such that it does not adversely affect the transport of fluid to the absorbent system 44 or the storage of fluid within the absorbent system 44.

Furthermore, while FIGS. 1-5 and FIGS. 6-8 depict only a single stabilizing layer, it is within the scope of the invention to include a plurality of stabilizing layers placed on top of one another or, along side of one another.

Furthermore, while FIGS. 1-5 and FIGS. 6-8 depict the presence of an absorbent system 44, it is contemplated that absorbent system 44 may be omitted. In this embodiment, the stabilizing layer 52 functions both to stabilize and also provides the liquid absorbing function and possibly other functions of the absorbent system 44, as described below in the section entitled "Main Body—Absorbent System". As such, in this embodiment, no separate absorbent system is required.

Main Body—Stabilizing Layer

In order to provide both ease of use as well as comfort and conformability, the stabilizing layer 52 has a Dry Stiffness Index of at least about 0.9 g/gsm (grams/grams per square meter) and a Wet Stiffness Loss of at least about 80 percent (%). In a preferred embodiment, the Dry Stiffness Index is at least about 1.0 g/gsm and, more preferably, greater than about 1.3 g/gsm, such as from about 1.3 g/gsm to about 2.5 g/gsm. Furthermore, in a preferred embodiment, the stabilizing layer has a Wet Stiffness Loss of at least about 90%. The methods for determining Wet Stiffness Loss and Dry Stiffness Index are set forth in detail herein.

Although not required, according to one embodiment of the invention the stabilizing layer 52 is selected to be slowly dispersible in water. By "slowly dispersible" it is meant that when tested according to the Water Dispersibility Test set forth herein, the Water Dispersibility Time is from about 20 seconds to about 500 seconds, more preferably from about 30 seconds to about 250 seconds.

The ranges of Dry Stiffness Index and Wet Stiffness Loss for the stabilizing layer 52 may be achieved through various means. For example, in order to provide the stabilizing layer 52 with stiffness that is reduced by interaction with moisture, the stabilizing layer 52 may include a water-dispersible or water-soluble material, such as a thermoplastic or latex polymeric binder. To further provide sufficiently high dry stiffness, the polymeric binder desirably has a high glass transition temperature, $T_g$, such as greater than about 40° C., and more preferably greater than about 60° C. In a preferred embodiment of the invention, the stabilizing layer 52 includes a mixture of cellulosic fibers and a water soluble polymeric binder.

The polymeric binder may be a synthetic or natural polymer that is water-soluble and/or water-dispersible. Various chemistries of polymers may be suitable including, for example: vinyl polymers such as polyvinyl alcohol, polyvinyl pyrolidone, polyvinyl acetate or other polymers; acrylic polymers; polyalkylene glycols; polyurethanes, polyurethane-acrylics; polyester-polyurethanes; polyether-polyurethanes polyacrylamides; polyureas; polysulfonates; poly(2-ethyl-2-oxazoline); proteins or protein hydrolyzate, such as an extract of milk, wheat or other cereals or of leguminous plants and of oleaginous plants; and derivatives of cellulose that have been rendered water-soluble and/or water-dispersible, such as hydroxyalkylcelluloses or cellulose polymers that are derived from the polymerization of rings of D-glucopyranose, D-glucose, D-galactose, D-mannose, D-xylose or other saccharides, polysaccharide derived from algae or plants, for example, starches, glycogen, cellulose, amylopectin, amylase, xylan, gum tragacanth, inulin, laminarin, and mannan, as well as chitin, glycogen, hyaluronic acid, and galactan; among other classes of polymers.

One particularly suitable polymer is a polyvinyl alcohol, such as partially hydrolyzed (88% hydrolyzed) polyvinyl alcohol (PVA) that is water soluble, e.g., CELVOL 203, commercially available from Celanese Corporation of Dallas, Tex. Another suitable binder is starch polymer available as VINAMUL Structurecote 1887 from National Starch and Chemical of Bridgewater, N.J.

The stabilizing layer 52 may also include a carrier onto which the binder is coated or otherwise formed. The carrier may comprise or consist essentially of material that can be rendered flexible when the stabilizing layer absorbs fluid and the binder interacts with the absorbed fluid. The carrier may be, for example, a fibrous material. The fibrous material may be a layer of fibers such as, for example cellulose fibers (e.g., pulp) or synthetic fibers such as polyolefin, polyester, polyamide and the like. The fibers may be rendered hydrophilic in order to render them readily treated with an aqueous solution or dispersion of binder.

The stabilizing layer 52 preferably comprises a concentration of water-dispersible or water-soluble binder in a weight percentage in the stabilizing layer that is sufficiently high to provide the required Wet Stiffness Loss and Dry Stiffness Index. In a preferred embodiment of the invention, the stabilizing layer includes a weight percentage of water-soluble or water dispersible binder in the amount of from about 10% to about 50% by weight, and more preferably from about 15% to about 40% by weight. In this preferred embodiment of the invention the stabilizing layer further includes a weight percentage of cellulosic fibers from about 90% to about 50% and more preferably from about 75% to about 60% by weight.

The stabilizing layer 52 is desirably a free-standing layer, i.e., a layer that is, for example, placed against and optionally laminated or adhered to other material layers in the sanitary napkin 20. The stabilizing layer 52 may be structured and arranged so that it can be readily separated from other layers (e.g., such as by pulling it apart from such other layers) of the sanitary napkin. It is also within the scope of the invention for the stabilizing layer 52 to be firmly adhered to another layer of the sanitary napkin 20. For example, the stabilizing layer may include an adhesive, such as a hot melt or thermoplastic adhesive, as long as the adhesive does not cause the Dry Stiffness Index and Wet Stiffness Loss of the stabilizing layer to fall outside the specified ranges.

The stabilizing layer 52 may include other components as long as the Dry Stiffness Index and Wet Stiffness Loss remain within the specified ranges. Such other components include dyes, fragrances, resins and the like. In order to increase the fluid absorbency of the stabilizing layer, in one embodiment, it is desirable for the stabilizing layer to include super absorbent polymers (SAP), e.g., crosslinked swellable acrylic polymer particles or fibers. For example, the stabilizing layer may include a percentage of SAP that is from about 5% to about 30%, such as from about 5% to about 15% of SAP.

However, because the introduction of SAP in the stabilizing layer may result in a relatively lengthy time to dry (e.g., after an aqueous solution of polymeric binder is applied to the carrier), it may be desirable in certain embodiments to include only low concentrations of SAP, or exclude SAP entirely from the stabilizing layer 52. As such, in this alternative embodiment, the concentration of SAP in the stabilizing layer 52 is less than about 15%, more preferably less than 5%, and most preferably the SAP is excluded from the stabilizing layer 52.

The stabilizing layer 52 desirably has a weight relative to the total weight of the sanitary napkin (i.e., a weight fraction) that is high enough to permit easy stabilizing of the sanitary napkin but not so high that it makes the dry sanitary napkin 20 uncomfortable when it is first positioned against the body. As such, the weight fraction of the stabilizing layer 52 to the total weight of the napkin may be from about 5% to about 30%, such as from about 10% to about 20%. As such, the stabilizing layer 52 may have a basis weight that is from about 30 gsm to about 200 gsm, more preferably about 30 gsm to about 100 gsm.

One particularly suitable stabilizing layer 52 in accordance with the present invention is a layer that is 80% air-laid pulp by weight and 20% PVOH binder by weight, the stabilizing layer 52 has a basis weight of about 70 gsm.

If the stabilizing layer 52 is arranged between the cover layer 42 and the absorbent system 44, the material comprising the stabilizing layer 52 should be selected such that it readily transmits fluid to the absorbent system 44. For example, the stabilizing layer 52 may comprise a nonwoven material including a blend or mixture of synthetic and/or cellulosic fibers. Suitable specific material compositions will be apparent to those skilled in the art.

Main Body—Cover Layer

The cover layer 42 may be a relatively low density, bulky, high-loft non-woven web material. The cover layer 42 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 42 has a basis weight in the range of about 10 gsm to about 75 gsm.

Bi-component fibers may be made up of a polyester layer and a an polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polyester or bi-component fibers, the cover layer 42 may be treated with a surfactant to impart the desired degree of wettability.

In one preferred embodiment of the present invention the cover is made from a spunlace nonwoven material having from about 0 to about 100% polyester and from about 0 to about 100% rayon. The spunlace material may also be made from about 10% to about 65% rayon and from about 35% to about 90% polyester. In lieu of, and/or in combination with the polyester, polyethylene, polypropylene or cellulosic fiber may be used with the rayon. Optionally, the material used for the cover layer may include binders such as thermoplastic binders and latex binders.

The term "nonabsorbent fibers" as used herein means fibers that do not retain any fluid within the polymer matrix of the fiber body itself. Examples of suitable nonabsorbent fibers include polypropylene, polyester, polyethylene and bicomponent fibers made from combinations of polypropylene, polyester and polyethylene.

The surface of the nonabsorbent fibers may be rendered "permanently wetable" (hydrophilic) via suitable surface finishing compositions, such as appropriate surfactants as well as internal surfactants. The term "permanently wetable" as used herein means that the surface of the fibers retain their wettable characteristics after the spunlacing process. Specific examples of fibers whose surface is permanently wettable are commercially available and are set forth below in the examples.

Preferably spunlace materials according to the present invention include at least 20% of nonabsorbent fibers by weight that have a fiber surface that is permanently wettable, more preferably at least 35% nonabsorbent fibers by weight that have a fiber surface that is permanently wettable and most preferably at least 50% nonabsorbent fibers by weight that have a fiber surface that is permanently wettable.

"Composed substantially entirely of nonabsorbent fibers" as used herein means that preferably at least 90% of the fibers by weight in the spunlace cover material are nonabsorbent, more preferably at least 95% by weight are nonabsorbent, and most preferably 100% of the fibers by weight are nonabsorbent.

In another specific embodiment the cover material is a spunlace nonwoven material that contains between about 10% and 90% polypropylene fibers by weight and between 90% and 10% polyester fibers by weight, more preferably between about 35% and 65% polypropylene fibers by weight and 65% and 35% polyester fibers by weight.

In those embodiments of the spunlace cover material wherein the spunlace cover includes a preformed web introduced prior to hydro entangling, the preformed web preferably makes up about 10% to about 50% by weight of the total cover weight. The preformed web material preferably has a basis weight in the range of about 5 gsm to about 20 gsm, and more preferably from about 10 gsm to about 15 gsm. The preformed is also preferably constructed from a nonabsorbent material such as polyethylene or polypropylene.

In the those embodiments of the present invention where the cover material is a spunlace material the cover preferably has a total basis weight of about 30 gsm to about 80 gsm and more preferably about 40 gsm to about 60 gsm.

Alternatively, the cover layer 42 can also be made of polymer film having large pores. Because of such high porosity, the film accomplishes the function of quickly transferring body fluid to the inner layers of the absorbent system. Apertured co-extruded films such described in U.S. Pat. No. 4,690,679 and available on sanitary napkins sold by Johnson & Johnson Inc. of Montreal, Canada could be useful as cover layers in the present invention.

The cover layer 42 may be embossed to the remainder of the absorbent system 44 in order to aid in promoting hydrophilicity by fusing the cover to the next layer. Such fusion may be effected locally, at a plurality of sites or over the entire contact surface of cover layer 42 and absorbent system 44. Alternatively, the cover layer 42 may be attached to the absorbent system 44 by other means such as by adhesion.

Main Body—Barrier Layer

Barrier layer 50 comprises a liquid-impervious film material so as to prevent liquid that is entrapped in the absorbent system 44 from egressing the sanitary napkin and staining the wearer's undergarment. The barrier layer 50 is preferably made of polymeric film, although it may be made of liquid impervious, air-permeable material such as repellent-treated non-woven or micropore films or foams.

Positioning adhesive 58 may be applied to a garment facing side of the barrier layer for securing the napkin 20 to the garment during use. The positioning adhesive 58 may be covered with removable release paper 60 so that the positioning adhesive is covered by the removable release paper 60 prior to use.

The barrier layer may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 42 and the barrier layer 50 are joined along their marginal portions so as to form an enclosure or flange seal that maintains the positioning layer and optionally places absorbent layer 44 captive. The joint may be made by means of adhesives, heat-bonding, ultrasonic bonding, radio frequency sealing, mechanical crimping, and the like and combinations thereof.

Main Body—Absorbent System

The sanitary napkin 20 may include an optional absorbent system 44. As used herein the term absorbent system refers to any material or multiple material layers whose primary function is to absorb, store and distribute fluid especially menses that is discharged by the wearer and prevent the back flow of stored fluid towards the cover and contacting the wearer.

The absorbent system 44 may comprise a single layer of material or may comprise multiple layers. In one embodiment, the absorbent system 44 is a blend or mixture of cellulosic fibers and superabsorbent disposed in and amongst fibers of that pulp.

It is possible that the absorbent system 44 could be integrated with the cover and/or barrier such that there is essentially only a single layer structure or a two layer structure including the function of the multiple layers described herein. As mentioned above, it is also possible that the function of the absorbent layer is at least present in the stabilizing layer and, as such, no absorbent system distinct from the stabilizing layer is present.

Cellulosic fibers that can be used in the absorbent system 44 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material. The absorbent system 44 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

The absorbent system 44 may comprise a material manufactured by using air-laying means well known in the art. In a specific example, the absorbent system 44 is an air laid material made from cellulosic fibers, bonding materials and components that cannot form a bond (nonbonding materials) with the other component materials.

Examples of bonding materials include latex binders, thermoplastic particles or fibers that melt at the "process temperature" (as defined below), adhesives, or bicomponent fibers wherein at least a portion of the bicomponent fiber melts at the process temperature. The term "process temperature" as used herein means the highest temperature to which the material is subjected to during the air laying process. The process temperature may vary depending on the specific air laying process, and the process temperature is selected by those skilled in the art for a particular air laying process, however in order for a synthetic and/or bicomponent fiber to function as "bonding materials" herein they must have a melting temperature less than the selected process temperature. For example if an airlaid material includes polyethylene fibers having a melting temperature of 128° C. and polyester fibers having a melting temperature of 260° C. and the process temperature is selected to be 160° then the polyethylene fibers would function as bonding materials and the polyester fibers would function as nonbonding materials.

Examples of nonbonding materials include SAP (superabsorbent polymer), cellulosic fibers, and synthetic and bicomponent fibers having a melting temperature that is higher than the selected process temperature such that they will not melt and bond at the process temperature.

Specific examples of suitable airlaid materials include less than 50% cellulosic fibers by weight, less than 20% bonding materials by weight and greater 30% nonbonding materials by weight. Specific airlaid materials according to the present invention have less than 20% bonding materials by weight, more preferably less than 15% bonding materials by weight and most preferably between about 3%-10% bonding materials by weight. Specific examples of airlaid materials according to the present invention may also include an optional carrier material arranged on either or both surfaces of the cellulosic mixture. For purposes of the weight percentages provided for bonding materials and nonbinding materials herein the carrier should not be included in such calculations.

Specific examples of suitable airlaid materials also preferably have a basis weight in the range of about 50 gsm to about 600 gsm and a density in the range of about 0.03 g/cc to about 0.2 g/cc. If a latex binder is used as the binding material the $T_g$ of the latex material should be less than 25° C. Specific examples of suitable airlaid materials have a thickness less than 5 mm and more preferably less than 3 mm. If a binding fiber, such as a bicomponent fiber, is used as the binding material then the binding fiber should have a denier per filament of equal to 3 dpf or less.

A specific airlaid based absorbent system for use in absorbent articles according to the present invention includes a pair of wetlaid tissue carriers (17 grams per square meter basis weight, produced by Cellu Tissue Holdings Inc., East Hartford Conn.) with a mixture of wood pulp, polyester fibers and Sumitomo SA70 SAP disposed between the carriers. The pulp is bleached softwood pulp, produced by a kraft process. Approximately 20% of the pulp has been mercerized. The total composite has a basis weight of 250 gsm and contains 40% superabsorbent (Sumitomo SA70) and 6% polyester staple fibers (3.0 DPF by 1.5" inch cut length, KOSA #611153, Salisbury, N.C.). The airlaid machine which produces this material consists of unwinds, hammermills, airlaid forming heads, SAP dispensers, and a heated calendering station with a pattern roll and a flat anvil roll. Fluff pulp mixed with SAP and PET fibers in the air-laid forming chambers is cast on the first carrier tissue with a strong vacuum underneath. Before the composite reaches the calendering station another tissue is introduced from the top. It is then calender between the flat anvil roll and the patterned calendar roll. The calendar roll pattern consists of a matrix of diamonds with lines between the diamonds raised to a height of 0.075". The diamonds have a major axis of 0.325" and a minor axis of 0.201". The diamonds have a spacing of 0.046" between them. After the heat emboss calendering, the embossed area between the diamonds had a density of about 0.4 g/cc and the diamond shaped raised area has density of 0.15 g/cc.

Other Structures

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

The absorbent article of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof, hot melt adhesives based on suitable block copoylmers—suitable block copolymers for use in the invention include linear or radial co-polymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Where adhesive is used, a release strip may be applied to protect the adhesive on the absorbent article prior to attaching the absorbent article to the crotch. The release strip can be formed from any suitable sheet-like material adheres with sufficient tenacity to the adhesive to remain in place prior to use but which can be readily removed when the absorbent article is to be used. Optionally, a coating may be applied to release strip to improve the ease of removabilty of the release strip from the adhesive. Any coating capable of achieving this result may be used, e.g., silicone.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like material, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated herein include asymmetrical and symmetrical absorbent articles having parallel longitudinal edges, dog bone- or peanut-shaped, as well as articles having a tapered construction for use with thong-style undergarments.

Test Procedures for Stabilizing Layer

To determine the suitability of a layer to serve as a stabilizing layer, according to the test method set forth herein, a minimum of six (6) samples of the layer material to be tested are required.

Procedure for Measuring Dry Stiffness Index and Wet Stiffness Loss of the Stabilizing Layer In order to provide both ease of use as well as comfort and conformability, the stabilizing layer 52 employed in the present invention has a Dry Stiffness Index of at least about 0.9 g/gsm (grams/grams per square meter) and a Wet Stiffness Loss of at least about 80 percent (%). In a preferred embodiment, the Dry Stiffness Index is at least about 1.0 g/gsm and, more preferably, greater than about 1.3 g/gsm, such as from about 1.3 g/gsm to about 2.5 g/gsm. Furthermore, in a preferred embodiment, the stabilizing layer has Wet Stiffness Loss of at least about 90%. The methods for determining Wet Stiffness Loss and Dry Stiffness Index are set forth in detail below.

"Dry Stiffness Index" is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform, which is 102.0 mm by 102.0 mm by 6.35 mm having an 18.75 mm diameter orifice. The lap edge of the orifice should be at a 45 degree angle to a depth of 4.75 mm;

2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;

3. A force-measurement gauge and more specifically an Instron inverted compression load cell. The load cell has a load range of from about 0.0 to about 2000.0 g;

4. An actuator and more specifically the Instron Model No. 1122 having an inverted compression load cell. The Instron 1122 is made by the Instron Engineering Corporation, Canton, Mass.

In order to perform the procedure for this test, as explained below, three representative layer material samples are required. If the layer sample is to be taken from an absorbent article having a plurality of layers, then the constituent layers of the article should first be carefully separated to isolate the layer to be tested. If the constituent layers of the article are adhered to one anther by an adhesive than a suitable solvent may be used to separate the layers of the absorbent article. Suitable solvents for this purposes are well known to those skilled in the art.

Three 37.5 mm by 37.5 mm test specimens are cut from the material to be tested. The test specimens should not be folded or bent by the test person, and the handling of specimens must be kept to a minimum and to the edges to avoid affecting flexural-resistance properties.

The procedure for the CIRCULAR BEND PROCEDURE is as follows. The specimens are conditioned by leaving them in a room that is 21° C., +/−1° C. and 50%, +/−2.0%, relative humidity for a period of two hours.

The weight of each cut test specimen is measured in grams and divided by a factor of 0.0014. This is the basis weight in units of grams per square meter (gsm). The values obtained for basis weight for each of the test specimens is averaged to provide an average basis weight (BW). This average basis weight (BW) may then be utilized to determine Dry Stiffness Index as set forth below.

A test specimen is centered on the orifice platform below the plunger such that the body facing layer of the test specimen is facing the plunger and the barrier layer of the specimen is facing the platform. The plunger speed is set at 50.0 cm per minute per full stroke length. The indicator zero is checked and adjusted, if necessary. The plunger is actuated. Touching the test specimen during the testing should be avoided. The maximum force reading to the nearest gram is recorded. The above steps are repeated until all of three test specimens have been tested. An average is then taken from the three test values recorded to provide an average dry stiffness. The average dry stiffness is divided by the average basis weight (BW), and this quotient is recorded as "Dry Stiffness Index" and has units of g/gsm.

To determine Wet Stiffness Loss, the CIRCULAR BEND PROCEDURE is repeated on each of the samples above after applying a mass of deionized water evenly across the sample. The deionized water is applied by suspending the sample over the top of a beaker containing boiling water and the water is allowed to condense on the sample. The sample is removed and the mass of the sample with the added moisture is recorded. If the mass has increased by 50% to 56% from its original (dry) mass, the sample is removed and again tested using the CIRCULAR BEND PROCEDURE. If the mass of the sample has increased less than 50%, the sample is returned to its suspended state above the beaker of boiling water to accumulate more moisture. If the sample has accumulated more than 56% of moisture, the sample is discarded. This process is repeated until three samples having 50% to 56% moisture have been measured. Each moistened sample is tested using the CIRCULAR BEND PROCEDURE. An average is then taken from the three test values recorded to provide an average wet stiffness. Wet Stiffness Loss is determined by dividing average wet stiffness by average dry stiffness and expressed as a percentage.

Procedure for Measuring Water Dispersibility Time of the Stabilizing Layer

Water Dispersibility Time is determined by a WATER DISPERSIBILITY PROCEDURE to determine the time required for a layer of material to disperse or disintegrate in water as follows. Three fresh 37.5 mm by 37.5 mm material test specimens are required to determine the water dispersibility time of the stabilizing layer.

The apparatus necessary for the WATER DISPERSIBILITY PROCEDURE includes:

1. A Lab Line Instruments Junior Orbit Shaker #3250 (¾" orbit), commercially available from Lab Line Instruments Inc., Melrose Park, Ill.;

2. A 2000 ml flask;

3. A shaker platform and clamps for the flasks;

4. A timer/stopwatch, accurate to 0.01 seconds;

5. A balance, sensitive to 0.001 grams; and

6. Forceps.

Each sample to be tested is weighed using the balance and initial mass is recorded. 1600 ml of deionized water is added to a flask and the flask is placed on the shaker platform. The orbital shaker is powered and the shaking rate is set at 200 rpms. While holding the stopwatch in one hand, the test sample is placed over the mouth of the flask and dropped into the center of the spinning vortex of water in the flask containing the water. At the moment the sample touches the water, the operator starts the stopwatch while carefully observing the sample. Water dispersibility time is recorded as the time elapsed for "complete dispersion." The result is expressed in seconds (s). "Complete dispersion" as used herein means that the mixture of water and dispersed sample can be poured through a 4 mm×4 mm metal mesh screen without any substantial portions of the sample being trapped in the screen.

Test Procedures for Sanitary Articles

Sanitary napkins according to the present invention include a first portion 54 located outside the dimensions of the stabilizing layer and a second portion 56 located within the dimensions of the stabilizing layer. Preferably, the first portion 54 of the sanitary napkin, i.e. the portion located outside the dimensions of the stabilizing layer, is highly flexible in the dry state. "Highly flexible" as used herein means having a flexural resistance, i.e. an MCB Stiffness as defined herein, of less than 400 g, preferably less than 250 g and most preferably less than 150 g. Preferably, the second portion 56 of the sanitary napkin, i.e. the portion located within the dimensions of the stabilizing layer, is sufficiently stiff in the dry state to enable the user to easily handle and place the napkin in the undergarment prior to use. "Sufficiently stiff" as used herein means an MCB Stiffness of greater than 400 g. The method for determining the MCB Stiffness of the first and second portions, 54 and 56, of the absorbent article is set forth below.

Procedure for Measuring Modified Circular Bend Stiffness (MCB) of a Sanitary Article Modified Circular Bend Stiffness (MCB) is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform, which is 102.0 mm by 102.0 by 6.35 mm having an 18.75 mm diameter orifice. The lap edge of the orifice should be at a 45 degree angle to a depth of 4.75 mm;

2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;

3. A force-measurement gauge and more specifically an Instron inverted compression load cell. The load cell has a load range of from about 0.0 to about 2000.0 g;

4. An actuator and more specifically the Instron Model No. 1122 having an inverted compression load cell. The Instron 1122 is made by the Instron Engineering Corporation, Canton, Mass.

In order to perform the procedure for this test, as explained below, three representative product samples for each article to be tested are necessary. Two 37.5 mm by 37.5 mm test specimens are cut from each of the three product samples at corresponding locations. One sample from each product should be taken from within the dimensions of the stabilizing layer and one sample from each product should be taken outside the dimensions of the stabilizing layer.

Prior to cutting the test specimens any release paper or packaging material is removed from the product sample and any exposed adhesive, such as garment positioning adhesive, is covered with a non-tacky powder such as talc or the like. The talc should not affect the MCB measurement.

The test specimens should not be folded or bent by the test person, and the handling of specimens must be kept to a minimum and to the edges to avoid affecting flexural-resistance properties.

The procedure for the CIRCULAR BEND PROCEDURE is as follows. The specimens are conditioned by leaving them in a room that is 21° C., +/−1° C. and 50%, +/−2.0%, relative humidity for a period of two hours.

A test specimen is centered on the orifice platform below the plunger such that the body facing layer of the test specimen is facing the plunger and the barrier layer of the specimen is facing the platform. The plunger speed is set at 50.0 cm per minute per full stroke length. The indicator zero is checked and adjusted, if necessary. The plunger is actuated. Touching the test specimen during the testing should be avoided. The maximum force reading to the nearest gram is recorded. The above steps are repeated until all of three test specimens have been tested. An average is then taken from the three test values recorded to provide an average MCB Stiffness.

The above procedure should be separately performed for the article specimens taken within the dimensions of the stabilizing layer and the article specimens taken outside the dimensions of the stabilizing layer. In this manner, an average MCB Stiffness is calculated for the first portion of the article (i.e. the portion located outside the dimensions of the stabilizing layer) and an average MCB Stiffness is calculated for the second portion of the article (i.e. the portion located within the dimensions of the stabilizing layer).

Procedure for Measuring the Thickness of a Sanitary Article

The thickness measurement procedure described below should be conducted on three product samples prior to conducting the MCB test described above and after the product samples have been removed from any packaging, any release paper has been removed, and after the product has been powdered with talc or the like. The thickness measurement of the product should be taken within the first portion of the absorbent article, i.e. the portion located outside the dimensions of the stabilizing layer.

Sanitary napkins according to the present invention are preferably thin. Sanitary napkins according to the present invention preferably have a thickness of less than 4.0 mm, more preferably less than 3.0 mm, and most preferably less than 2.5 mm. The procedure for measuring the thickness of an absorbent article is described below.

The apparatus required to measure the thickness of the sanitary napkin is a footed dial (thickness) gauge with stand, available from Ames, with a 2" diameter foot at a pressure of 0.07 psig and a readout accurate to 0.001". A digital type apparatus is preferred. If the sanitary napkin sample is individually folded and wrapped, the sample is unwrapped and carefully flattened by hand. The release paper is removed from the product sample and it is repositioned back gently across the positioning adhesive lines so as not to compress the sample, ensuring that the release paper lies flat across the sample. Flaps (if any) are not considered when taking the thickness reading.

The foot of the gauge is raised and the product sample is placed on the anvil such that the foot of the gauge is approxi mately centered on the location of interest on the product sample. When lowering the foot, care must be taken to prevent the foot dropping onto the product sample or undue force being applied. A load of 0.07 p.s.i.g. is applied to the sample and the read out is allowed to stabilize for approximately 5

The stabilizing layer samples suitable for use in the present invention and comparative samples were tested according to the test methods described in the "Test Procedures for Stabilizing Layer" section above, the results of which are set forth in the table provided below.

|  | Inventive Sample #1 | Inventive Sample #2 | Comparative Sample #1 | Comparative Sample #2 | Comparative Sample #3 |
|---|---|---|---|---|---|
| Basis Weight (gsm) | 63 | 66 | 224 | 90 | 30 |
| Dry Stiffness of Stabilizing Layer (g) | 68.1 | 102 | 101 | 79.1 | 9.8 |
| Dry Stiffness Index (g/gsm) | 1.08 | 1.55 | 0.45 | 0.88 | 0.33 |
| Moisture add-on (%) | 54 | 56 | 54 | 51 | 52 |
| Wet Stiffness of Stabilizing Layer (g) | 4.6 | 7.7 | 75.4 | 30.4 | 2.1 |
| Wet Stiffness Loss (%) | 93 | 93 | 25 | 61 | 78 |
| Binder Tg (° C.) | >85 | 85 | N/A | N/A | N/A |
| Water dispersibility Time (s) | 153 | 141 | 18 | Does not disperse | Does not disperse | seconds. The thickness reading is then taken. This procedure is repeated for at least three article samples and the average thickness is then calculated.

Examples of Inventive Stabilizing Layers

Specific examples of inventive stabilizing layers are described below. Comparative Samples are also provided.

Inventive Stabilizing Layer #1

A stabilizing layer suitable for use in the invention described herein was made by spraying 65 gsm of a solution of 20% weight percent starch based binder (VINAMUL Structurecote 1887 commercially available from National Starch and Chemical, Bridgewater, N.J.) onto a layer of airlaid pulp (Buckeye Vicell X-824, commercially available from Buckeye Technologies, Memphis, Tenn.) having a basis weight of 65 gsm. The sprayed layer was allowed to dry. After the water in the binder dries off, the concentration of binder in the resulting stabilizing layer was about 20% by weight. This concentration was calculated as follows: concentration of binder (%)=weight of binder (g)/weight of the substrate to which the binder is applied (g).

Inventive Stabilizing Layer #2

A stabilizing layer suitable for use in the invention described herein was made by spraying a solution of 24% weight percent PVA binder (CELVOL 203 commercially available from Celanese Corporation, Dallas, Tex.) onto a layer of air-laid pulp (Buckeye Vicell X-824, commercially available from Buckeye Technologies, Memphis, Tenn.) having a basis weight of 65 gsm. The sprayed layer was allowed to dry. The concentration of binder in the resulting stabilizing layer was 20% by weight.

Comparative Sample #1 Calendared NovaThin™ Absorbent Core with 25% SAP and about 75% cellulosic fiber, commercially available from EAM Corporation of Jessup, Ga.

Comparative Sample #2 A 90 gsm version of Buckeye Vizorb™ air-laid nonwoven material, commercially available from Buckeye Technologies, Memphis, Tenn.

Comparative Sample #3 SCOTT C-Fold Professional Paper Towel, commercially available from Kimberly Clark of Neenah, Wis.

Example of Inventive Absorbent Article

A sanitary napkin according to the present invention was constructed including a two layer spunlace nonwoven cover having a top body facing layer of 56 gsm of PET fibers and a bottom 19 gsm rayon layer. The absorbent system arranged directly underneath the cover included two wetlaid tissue carriers (17 grams per square meter basis weight, produced by Cellu Tisue Holdings Inc., East Hartford Conn.) with a mixture of wood pulp, polyester fibers and Sumitomo SA70 SAP disposed between the layers. The pulp was bleached softwood pulp, produced by a kraft process. Approximately 20% of the pulp had been mercerized. The total absorbent had a basis weight of 250 gsm and contained 40% superabsorbent (Sumitomo SA70) and 6% polyester staple fibers (3.0 DPF by 1.5" inch cut length, KOSA #611153, Salisbury, N.C.). The airlaid machine which produced this material consisted of unwinds, hammermills, air-laid forming heads, SAP dispensers, and a heated calendering station with a pattern roll and a flat anvil roll. Fluff pulp mixed with SAP and PET fibers in the air-laid forming chambers is cast on the first carrier tissue with a strong vacuum underneath. Before the composite reached the calendering station another tissue is introduced from the top. It is then calendered between the flat anvil roll and the patterned calendar roll. The calendar roll pattern consisted of a matrix of diamonds with lines between the diamonds raised to a height of 0.075". The diamonds had a major axis of 0.325" and a minor axis of 0.201". The diamonds had a spacing of 0.046" between them. After the heat emboss calendering, the embossed area between the diamonds had a density of about 0.4 g/cc and the diamond shaped raised area has density of 0.15 g/cc. A barrier film layer was arranged below the absorbent system and consisted of a 0.9 mil polyethylene film produced by Pliant Corp, Pliant # 3492A. The absorbent facing surface of the barrier had 5.9 mg/sq in of Fuller 1023 adhesive applied to it to hold the product together. The absorbent facing surface of the cover had 2.6 mg/sq in of Fuller 1023 adhesive. The garment facing surface of the barrier was coated with 20 mg/sq inch of a pressure sensitive adhesive intended for panty attachment, Fuller 1417. A stabilizing layer having the composition described in Inventive Example 2 above was cut to a size of 40 mm (L1)×40 mm (W1). The stabilizing layer was positioned as a transverse strip, as shown in FIGS. 1-5 above, between the absorbent system and the barrier layer. The absorbent system a length La of 210 mm and width Wa of 65 mm. The stabilizing layer extended across about 12% of the absorbent system.

The average MCB Stiffness of the sanitary napkin, within the dimensions stabilizing layer, was measured to be about 450 g and the average MCB Stiffness of the sanitary napkin, outside the dimensions of the stabilizing layer, was measured to be about 101 g. The thickness of the sanitary napkin outside the dimensions of the stabilizing layer was measured to be 2.3 mm.

In view of the above absorbent articles according to the present invention provide the unique combination ease of handling and placement into position against the body, but also have high flexibility in use.

Applications of the absorbent article according to the present invention for sanitary and other health care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

I claim:

1. An absorbent article comprising:
a cover layer;
a barrier layer;
a stabilizing layer having dimensions, said stabilizing layer arranged between said cover layer and said barrier layer and has a Dry Stiffness Index of at least about 0.9 g/gsm and a Wet Stiffness Loss of at least about 80%;
a first portion located outside the dimensions of the stabilizing layer;
a second portion located within the dimensions of the stabilizing layer; and
wherein said first portion has an MCB Stiffness less than an MCB Stiffness of said second portion.

2. The absorbent article according to claim 1, wherein said first portion has an MCB Stiffness less than 250 g.

3. The absorbent article according to claim 1, wherein said first portion has an MCB Stiffness less than 150 g.

4. The absorbent article according to claim 1, wherein said first portion has a thickness of less than 4.0 mm.

5. The absorbent article according to claim 1, wherein said first portion has a thickness of less than 3.0 mm.

6. The absorbent article according to claim 1, wherein said first portion has a thickness of less than 2.5 mm.

7. The absorbent article according to claim 1, wherein said second portion has an MCB Stiffness greater than 400 g.

8. The absorbent article of claim 1, wherein said stabilizing layer has a Dry Stiffness Index of at least about 1.0 g/gsm.

9. The absorbent article of claim 1, wherein said stabilizing layer has a Dry Stiffness Index of at least about 1.3 g/gsm.

10. The absorbent article of claim 1, wherein said stabilizing layer has a Wet Stiffness Loss of at least about 90%.

11. The absorbent article of claim 1, wherein said stabilizing layer comprises a fibrous material and a polymeric binder, wherein said binder has a Tg greater than about 40° C.

12. The absorbent article of claim 11, wherein said binder is present in said stabilizing layer in a weight percentage that is from about 10% to about 50%.

13. The absorbent article of claim 12, wherein said binder is present in said stabilizing layer in a weight percentage that is from about 15% to about 40%.

14. The absorbent article of claim 12, wherein article further comprises an absorbent system arranged between said cover layer and said barrier layer; and
wherein said stabilizing layer extends across an area that covers from about 5% to about 50% of the absorbent system.

15. The absorbent article of claim 14, wherein said stabilizing layer extends across an area that covers from about 10% to about 25% of the absorbent system.

16. The absorbent article of claim 12, wherein said stabilizing layer has a water dispersibility time from about 20 seconds to about 500 seconds.

17. The absorbent article of claim 16, wherein said stabilizing layer has a water dispersibility time from about 30 seconds to about 250 seconds.

18. An absorbent article comprising:
a cover layer;
a barrier layer;
an absorbent system arranged between said cover layer and said barrier layer;
a stabilizing layer comprising a mixture of fibrous material and a water-soluble binder, said fibrous material present in the amount of from about 50% to about 90by weight and said water-soluble binder present in an amount of from about 10% to about 50% by weight;
a first portion located outside the dimensions of the stabilizing layer;
a second portion located within the dimensions of the stabilizing layer;
wherein said first portion has an MCB Stiffness less than an MCB Stiffness of said second portion; and
wherein said stabilizing layer has a Dry Stiffness Index of at least about 0.9 g/gsm and a Wet Stiffness Loss of at least about 80%.

19. The absorbent article according to claim 1, wherein said first portion has an MCB Stiffness less than 400 g.

* * * * *